(12) United States Patent
Stomp et al.

(10) Patent No.: US 6,872,544 B2
(45) Date of Patent: Mar. 29, 2005

(54) RAW MATERIAL SELECTION AND ANALYSIS FOR THE ISOLATION OF PROTEINASE INHIBITOR II FROM WHOLE POTATOES

(75) Inventors: Robert Stomp, Des Moines, IA (US); Hal G. Fallert, West Des Moines, IA (US)

(73) Assignee: Kemin Consumer Care, L.C., Des Moines, IA (US)

( * ) Notice: Subject to any disclaimer, the term of this patent is extended or adjusted under 35 U.S.C. 154(b) by 0 days.

(21) Appl. No.: 09/962,570

(22) Filed: Sep. 25, 2001

(65) Prior Publication Data

US 2003/0113829 A1 Jun. 19, 2003

(51) Int. Cl.$^7$ .............................. C12Q 1/37; C12N 9/00; C12N 9/50
(52) U.S. Cl. .......................... 435/23; 435/183; 435/219
(58) Field of Search ........................... 435/23, 183, 219

(56) References Cited

U.S. PATENT DOCUMENTS

| | | |
|---|---|---|
| 4,723,052 A | 2/1988 | Cochran |
| 5,434,343 A | 7/1995 | Johansen |
| 5,434,345 A | 7/1995 | Johansen |
| 6,133,033 A | 10/2000 | Secor et al. |

FOREIGN PATENT DOCUMENTS

| | | |
|---|---|---|
| WO | WO-09901474 | 1/1999 |
| WO | WO-0005406 | 2/2000 |

OTHER PUBLICATIONS

Walsh et al., "Two Kunitz–type proteinase inhibitors from potato tubers", Plant Physiology 97 (1) : 15–18 (1991).*
Mosolov et al., "Isolation from potato tubers of an inhibitor of trypsin and chymotrypsin", Biokhimiya 39 (5) : 956–963 (1974).*

Melville, J.C. and Ryan, C.A., "Chymotrypsin inhibitor I from potatoes", J. Biological Chem., 1972, 247: p. 3445–3453.

Ryan, C.L., "Purification and properties of a carboxypeptidase inhibitor from potatoes", J. Biol. Chem., 1974, 249: p. 5495–5499.

Bryant, J.; Green, T.R.; Gurusaddaiah, T.; and Ryan, C.L. "Proteinase inhibitor II from potatoes: Isolation and characterization of its protomer components", Biochemistry, 1976, 15: p. 3418–3424.

Ryan, C.A.; Kuo, T.; Pearce, G.; and Kunkel, R., "Variability in the concentration of three heat stable proteinase inhibitor proteins in potato tubers", American Potato Journal, 1976, 53: p. 443–454.

* cited by examiner

Primary Examiner—Sandra E. Saucier
(74) Attorney, Agent, or Firm—Kent A. Herink; Daniel A. Rosenberg; Davis Law Firm

(57) ABSTRACT

A method for assaying the proteinase inhibitor content of tissue of a plant. The proteinase inhibitor and other protein products are extracted from the plant tissue by preparing a mixture of solvent and comminuted plant tissue to form a solid fraction and a liquid fraction which contains the proteinase inhibitor and other protein products. The liquid fraction is heated to a temperature and for a time period sufficient to denature at least some of the other protein products without substantially denaturing the proteinase inhibitor. The denatured, undesired protein products are removed by centrifugation or filtering to prepare a clarified extract solution. The amount of proteinase inhibitor inhibitor in the clan ed extract is measured. If the assay is used in the selection of plant tissues for use in the extraction of proteinase inhibitor, plant tissues with a proteinase inhibitor content less than a pre-selected standard are rejected.

10 Claims, No Drawings

RAW MATERIAL SELECTION AND ANALYSIS FOR THE ISOLATION OF PROTEINASE INHIBITOR II FROM WHOLE POTATOES

BACKGROUND OF THE INVENTION

1. Field of the Invention

The present invention relates to an assay for the analysis and selection of potatoes having a high content of Proteinase Inhibitor II (PI2), and more specifically, to a fast and inexpensive assay of PI2 content of whole potatoes to be used as raw material in a process for extracting PI2 from the whole potatoes.

2. Background of the Prior Art

Proteins that inhibit proteolytic enzymes are often found in high concentrations in many seeds and other plant storage organs. Inhibitor proteins are also found in virtually all animal tissues and fluids. These proteins have been the object of considerable research for many years because of their ability to complex with and inhibit proteolytic enzymes from animals and microorganisms. The inhibitors have become valuable tools for the study of proteolysis in medicine and biology. Proteinase inhibitors are of particular interest due to their therapeutic potentials in controlling proteinases involved in a number of disorders such as pancreatitis, shock, and emphysema, and as agents for the regulation of mammalian fertilization. Potato tubers are a rich source of a complex group of proteins and polypeptides at potently inhibit several proteolytic enzymes usually found in animals and microorganisms. In particular, potato inhibitors are known to inhibit human digestive proteinases, and thus have application in the control of obesity and diabetes.

Proteinase inhibitors extracted from potatoes have been distinguished into two groups based on their heat stability. The group of inhibitors that is stable at 80° C. for 10 minutes have been identified as inhibitor I (mol. wt. 39,000) (Melville, J. C. and Ryan, C. A. Chymotrypsin inhibitor I from potatoes. *J. Biological Chem.*, 247: 3445–3453, 1972), carboxypeptidase inhibitor (CPI) (mol. wt. 4,100) (Ryan, C. L., Purification and properties of a carboxypeptidase inhibitor from potatoes. *J. Biol. Chem.* 249: 5495–5499, 1974), inhibitors IIa and IIb (mol. wt. 20,700) (Bryant, J., Green, T. R., Gurusaddaiah, T., Ryan, C. L. Proteinase inhibitor II from potatoes: Isolation and characterization of its protomer components. *Biochemistry* 15: 3418–3424, 1976), and inhibitor A5 (mol. wt. 26,000).

In 1972, Melville and Ryan (Melville et al.) reported a large-scale preparation for isolating Chymotrypsin Inhibitor I from potato tubers. According to the method of Melville and Ryan, potatoes were sliced with peels intact and soaked in a sodium dithionite solution, homogenized, and expressed through nylon cloth. The resulting juice was adjusted to a pH of 3, centrifuged at 1000×g for 15 minutes at 5° F. and the supernatant collected and fractionated with ammonium sulfate.

Purification was achieved through water washing and heat treatment whereby clear filtrates of heated fractions were pooled and lyophilized. Suspending the lyophilized powder in water, dialyzing it against water for 48 hours, and lyophilizing the resulting clear filtrate obtained a crude extract. Resuspended extract was then centrifuged and applied to a column of Sephadex G-75. Collected fractions containing the Inhibitor I were pooled, evaporated, and desalted on a column of Sephadex G-25. The resulting gel-filtered inhibitor product was determined to be approximately 90% Inhibitor I protein purified by dissociation on a Sephadex G-75 column and desalted on a column of Sephadex G-25.

The Ryan lab followed-up by reporting the isolation and characterization of Proteinase Inhibitor II in much the same manner as described for Inhibitor I (Bryant, J., Green, T. R., Gurusaddaiah, T., Ryan, C. L. Proteinase inhibitor II from potatoes: Isolation and characterization of its protomer components. *Biochemistry* 15: 3418–3424, 1976). Bryant et al. differentiated potato-derived proteinase inhibitors into two groups based on their respective stabilities to a temperature of 80° C. for 10 minutes. Proteinase Inhibitor I (PI1) is characterized as a tetrameric protein composed of four hybridized isoinhibitor protomer species having a molecular weight of 39,000, whereas PI2 is characterized as a dimeric inhibitor comprising four isoinhibitor promoter species having a molecular weight of 21,000.

The isolation of proteinase inhibitor proteins from potatoes is described in WO 99/01474. Proteins from potato tubers are extracted in soluble form in an aqueous/alcohol extraction medium, such as dilute formic acid and 20% ethanol. The alcohol extract is heated to a first temperature to denature most of the unwanted proteins and cooled to a second temperature to form a precipitate phase constituting the debris and a soluble phase that contains the heat stable proteinase inhibitor proteins. The heat stable proteinase inhibitor proteins are precipitated from the soluble phase by dialysis against a suitable dialysis medium, such as dilute formic acid.

The production of PI2 on a commercial scale will be benefited by the identification and use of whole potatoes as starting material that have a high level of PI2. Such raw material will increase the amount of PI2 obtained from a given amount of starting material, will increase the efficiency of the extraction and purification steps, will reduce the amount of waste material, and will lower the cost of the PI2 product. Additionally, the raw material chosen is preferably be readily available in production-scale (truckload) quantity, and contains PI2 in consistent concentration.

Researchers have previously characterized a number of varieties of potatoes according to their proteinase inhibitor content (Ryan, C. A.; Kuo, T.; Pearce, G.; Kunkel, R. Variability in the concentration of three heat stable proteinase inhibitor proteins in potato tubers. *American Potato Journal*, 53: 443–454. 1976). In the study, PI2 was purified using chromatography, as described in Bryant, et al, supra. In summary, the method uses radial diffusion quantitation which requires radial assay materials, including spotting media and standards. Antibodies developed from antibody serum used in the assay had to be independently developed in the researcher's laboratory. The assay requires almost three months to generate useful data. The paper reports that there was a positive correlation (a correlation coefficient of 0.70) of both PI1 and PI2 with total soluble protein and proposed that the proteinase inhibitors could be used as excellent markers for genetic studies for selecting high protein potato tuber varieties.

The known assay for PI2 is time-consuming, labor intensive, was demonstrated only at laboratory scales, and expensive. Selection criteria currently evaluated by the potato processing industry have included total starch, sugar, water, and protein contents, but not PI2 content. Contrary to the conclusion reported in the *American Potato Journal*, the present assay has shown that there is no substantial correlation between total protein content and PI2 content. There is a need for an assay for PI2 that is rapid and inexpensive, and which will accurately forecast the yield of PI2 when the tested raw materials are used in a commercial PI2 extraction facility.

SUMMARY OF THE INVENTION

The invention consists of an assay for the PI2 content of whole potatoes that is useful for screening raw material to be used in a commercially scaled process for the extraction and purification of PI2. A representative sample of whole raw potatoes is selected. The potatoes selected are diced and added to a blender or other comminuting device. Approximately 40% on a weight basis of extractant (93.1:5.4:1.5 DI $H_2O$/NaCl/formic acid (w/w/w)) is added to the blender. An antifoam agent may be added to reduce foaming of the mixture during processing. The mixture is comminuted, preferably by pulse-blending, until the largest pieces are reduced to relatively uniform size. The mixture is then comminuted or blended continuously until liquefied. The liquefied material is centrifuged to produce a pellet and supernatant. The contents of the centrifuge are filtered until approximately seventy percent of the total liquid fraction has been collected. The mass and volume of this liquid is accurately weighed and recorded. In a separate flask, the filtering and collection process is continued and any remaining liquid is collected, with the mass and volume being measured and recorded. The first liquid sample is transferred to a flask and heated while stirring for between approximately 30 and 180 minutes in a water bath held at between approximately 60 to 90° C., and preferably about 70° C., to denature proteins in the liquid sample other than PI2. The flask is removed from the water bath and chilled to between approximately 20 and 25° C., resulting in the formation of a precipitate of the denatured proteins that will settle to the bottom of the flask yet leave the PI2 in solution. A sample of the supernatant is decanted and centrifuged at approximately 10,000 g for approximately 10 min. The supernatant is analyzed for PI2 content using high performance liquid chromatography.

An object of the invention is to provide a quick, easy, and inexpensive assay for PI2 in whole potatoes to be used as raw material in a commercial facility for the extraction of PI2.

Another object of the invention is to provide an assay for PI2 to be used in selecting varieties of potatoes for use as raw material in a commercial facility for the extraction of PI2.

A further object of the invention is to provide an assay for PI2 in whole potatoes that is predictive of the amount of PI2 that can be extracted from the potatoes in a commercial facility for the extraction of PI2.

DETAILED DESCRIPTION OF THE INVENTION

The assay for PI2 content in whole potatoes begins with the selection of a representative sample of the lot of potatoes being assayed. The representative sample is diced and added to a blender, grinder, or other comminuting device. A mixture of an organic acid, preferably formic acid, and a salt, preferably sodium chloride, is added to the diced, raw potatoes. The mixture is subjected to comminution to reduce the particle size of the potato particles and extract soluble proteins. Centrifugation is used to remove solids and the liquid fraction is heated at a temperature sufficient to denature many of the potato proteins but not PI2. The solution is cooled to precipitate out the denatured proteins but not the PI2. The solution is again centrifuged to separate the insoluble denatured proteins and the liquid fraction is evaluated for PI2 content by HPLC.

Reverse Phase HPLC Method

The amount of PI2, Kunitz and carboxypeptidase inhibitors was measured using reverse phase HPLC. A Microsorb C-18 column (4.6 mm×250 mm, 5 $\mu$m particles with 300 Angstrom pore size; Varian Analytical Instruments) was used. Two mobile phase solvents were prepared, solvent A was 800 g deionized $H_2O$, 150 g acetonitrile, and 0.95 trifluoroacetic acid, and solvent B was 850 g acetonitrile and 0.85 g trifluoroacetic acid. Approximately 50 mg of the sample was added to 100 ml of solvent A. The sample was vortexed for 30 seconds, and then centrifuged at 10,000 rpm for 10 minutes. The supernatant was collected for RP-HPLC analysis. One hundred $\mu$l of the sample was injected into the column, with the pump set at 800–2500 psig, and a temperature of 30.0° C. The other flow rate, time, and solvent compositions are as set out in Table 1. The diode array of the detector was set at 220 nm.

TABLE 1

HPLC Conditions

| TIME | SOLVENT A | SOLVENT B | FLOW (ML/MIN) |
| --- | --- | --- | --- |
| 0 | 100% | 0% | 1.000 |
| 5 | 100 | 0 | 1.000 |
| 34 | 38 | 62 | 1.000 |
| 38 | 0 | 100 | 1.000 |
| 40 | 0 | 100 | 2.000 |
| 45 | 0 | 100 | 2.000 |
| 50 | 100 | 0 | 1.000 |
| 55 | 100 | 0 | 1.000 |

An external standard was prepared to construct a standard curve for calibration of the column. Five mg of BSA were dissolved in 10 ml of solvent A. Four volumes, i.e., 25, 50, 75, and 100 $\mu$, were injected into the column. A calibration curve was generated from the results.

Assay Procedure

A representative sample of whole raw potatoes is selected. The total sample size should be greater than about 2.0 kg to assure that the assay will be representative of the potato lot. Each potato is cut in half bilaterally lengthwise. One half of each potato is discarded. The remaining material is diced into cubes that are approximately 1 cm$^3$. The cubes are thoroughly mixed to make a composite sample. Approximately 500 g are weighed and added to a food blender, together with 200.0 g of extractant (93.1:5.4:1.5 DI $H_2O$/NaCl/ formic acid (w/w/w)). Four drops of Mazo DF (BASF) antifoam are added to the mixture. The mixture is pulse-blended until the largest pieces are reduced to relatively uniform size (~30 sec). The mixture is then liquefied for 10 min.

The liquefied material is poured into a sufficient number of 250 ml centrifuge tubes to contain the entire volume and the tubes are centrifuged at 10,000 g for 20 min. Using a Buchner funnel and vacuum source, the supernatant is filtered through No.4 Whatman filter paper. The solids are added back filtering is continued until no less than 400 ml have been collected. The mass and volume of this liquid are accurately measured and recorded. In a separate flask, filtration and collection are continued with any remaining liquid and the mass and volume of any remaining liquid collected is recorded. The first liquid sample (~400 ml) is transferred to an Erlenmeyer flask and a stir bar is added. The flask is placed in a heated water bath held at 70° C. and the material is heated for 60 min while stirring. Next, the flask is removed from the water bath and chilled to 25° C.

A precipitate forms and settles to the bottom of the flask. Two ml of the supernatant is collected and centrifuged at 10,000 g for 10 min. The supernatant is analyzed for PI2 content by the previously described HPLC method.

The PI2 content of the potatoes is calculated using the following formula:

$$\frac{PI2 \text{ in raw material}}{(\text{mg } PI2/\text{kg potato})} = \frac{[PI2 \text{ determined by HPLC (mg/ml)}] * [\text{Total liquid collected (ml)}]}{\text{Mass of potatoes ground (kg)}}$$

EXAMPLE 1

Whole, raw potatoes are being used as feedstock for the isolation of proteinase inhibitor. To determine which varieties and sources of potatoes would provide a high level of PI2 on a consistent basis, potatoes from a variety of sources were assayed. The potatoes examined showed large variability with regard to PI2 content. Results of the assay are presented in Table 2. While numerous sources offered potatoes that attained the 100 mg/k target, Lot I consistently delivered potatoes that exceeded the target.

TABLE 2

Survey of Potatoes from a Variety of Sources

| Proteinase Inhibitor Raw Material Screening | HPLC area 1 | HPLC area 2 | mg PI2/100 ml | ml recovered | Kg raw | mgPI2/kg |
|---|---|---|---|---|---|---|
| Lot A | 1438 | 1769 | 7.6 | 497.9 | 0.50 | 30.1 |
| Lot B (Russet) | 1500 | 2556 | 9.3 | 484.5 | 0.50 | 44.7 |
| Lot C | 3000 | 6249 | 19.7 | 297.9 | 0.50 | 72.6 |
| Lot D (Russet Burbank) | 3263 | 6671 | 21.1 | 405.2 | 0.50 | 126.0 |
| Lot E (Russet) | 1590 | 2322 | 9.0 | 501.9 | 0.50 | 45.1 |
| Lot F (Russet Burbank) | 4120 | 3205 | 15.9 | 472.5 | 0.50 | 104.9 |
| Lot G (Russet Norkotah) | 2972 | 2824 | 12.8 | 489.9 | 0.50 | 80.2 |
| Lot H (Norkotah) | 1056 | 955 | 5.1 | 488.7 | 0.50 | 5.2 |
| Lot I (Russet Burbank) | 3495 | 7097 | 22.5 | 452.7 | 0.50 | 215.7 |

From this study, pilot grinding using Norkotah, and Russet Norkotah varieties was discontinued. Follow-up assays were performed using predominantly the source of Lot I, to verify source consistency.

TABLE 3

Pilot Plant-Raw Material Assay Data

| Sample | Area | PI2 (mg/ml) | liquid | solid | yield mg/kg |
|---|---|---|---|---|---|
| Raw a | 10592.9 | 0.24 | 452.7 | 179.5 | 215.7 |
| Raw b | 7572.3 | 0.18 | 449.0 | 181.5 | 158.0 |
| Raw c | 11066.5 | 0.29 | 453.1 | 171.2 | 266.5 |
| Raw d | 11994.8 | 0.31 | 465.2 | 167.9 | 290.7 |
| Raw e | 12521.2 | 0.32 | 459.8 | 159.1 | 296.9 |
| Raw f | 16046.7 | 0.39 | 456.1 | 161.9 | 358.1 |
| Raw g | 8477.4 | 0.24 | 473.5 | 172.5 | 230.0 |
| Raw h | 8258.7 | 0.24 | 450.6 | 178.8 | 214.9 |
| Raw i | 5680.0 | 0.19 | 461.1 | 158.9 | 172.9 |
| Raw j | 7320.7 | 0.22 | 470.1 | 148.7 | 206.8 |
| Raw k | 9116.6 | 0.26 | 464.3 | 155.5 | 237.2 |
| Raw l | 7355.9 | 0.22 | 487.3 | 161.5 | 215.1 |
| Raw m | 12472.0 | 0.32 | 492.9 | 174.5 | 317.3 |
| Raw n | 9214.1 | 0.26 | 458.0 | 188.1 | 235.8 |
| Raw o | 8252.0 | 0.24 | 490.8 | 150.4 | 234.0 |
| Raw p | 8604.9 | 0.25 | 488.8 | 149.9 | 239.8 |
| Raw q | 9889.2 | 0.27 | 490.6 | 165.7 | 265.7 |
| Raw r | 8307.7 | 0.24 | 477.7 | 146.3 | 228.8 |
| Raw s | 7454.5 | 0.22 | 485.9 | 177.3 | 216.3 |
| Raw t | 5122.5 | 0.18 | 472.3 | 178.4 | 166.7 |
| Raw u | 5859.0 | 0.19 | 447.7 | 159.9 | 171.1 |
| Raw v | 5177.2 | 0.18 | 455.4 | 184.3 | 161.7 |
| Raw w | 6627.8 | 0.21 | 488.5 | 166.1 | 201.5 |
| Raw x | 4771.1 | 0.17 | 469.5 | 166.9 | 159.2 |
| Raw y | 7578.4 | 0.23 | 464.9 | 157.0 | 209.3 |
| Raw z | 6746.7 | 0.21 | 483.1 | 170.6 | 201.6 |
| Raw aa | 7768.5 | 0.23 | 485.5 | 181.0 | 222.2 |
| Raw bb | 6848.1 | 0.21 | 479.4 | 146.5 | 201.9 |
| Raw cc | 7939.3 | 0.19 | 483.4 | 168.4 | 188.5 |
| Raw dd | 7407.2 | 0.18 | 497.8 | 147.1 | 183.9 |
| Raw ee | 5982.1 | 0.16 | 491.5 | 166.2 | 154.6 |
| Raw ff | 5295.8 | 0.14 | 483.0 | 163.2 | 139.2 |
| Raw gg | 8758.2 | 0.21 | 483.0 | 163.2 | 203.6 |

Table 3 presents the raw material analysis for pilot studies using predominantly Russet Burbank potatoes sourced from the source of Lot I of Table 2. The overall average yield for pilot quantity raw materials assayed was 217 mg/kg. Potatoes from the Lot I source taken alone averaged 221 mg/kg, and all other varieties taken together averaged 189 mg/kg. This represented an average PI2 content of 85.5% in non-Lot I sources, relative to the average Lot I source content, over the sample set examined.

EXAMPLE 2

In addition to varietal and supplier considerations, pilot runs were performed using different sized potatoes (referred to as 'count'). Table 4 presents average PI2 yields obtained using the assay of the present invention normalized to the maximum yield. Averages were taken using data from single suppliers of single varieties so that the results can be directly compared. The data shows that 90 count-size potatoes have exhibited the maximum PI2 yield on a mg/kg basis. It should be noted, however, that the count sizes of potatoes used for starting materials is not expected to substantially affect the commercial extraction process.

TABLE 4

Count-Size Study Using Russet Burbank Variety

| raw 90 | 100.00% |
|---|---|
| raw 100 | 93.28% |
| raw 110 | 97.26% |

TABLE 4-continued

Count-Size Study Using Russet Burbank Variety

| | |
|---|---|
| raw 120 | 88.27% |

The foregoing description comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention.

What is claimed is:

1. A method for assaying, without dialyzing, the proteinase inhibitor content of tissue of a plant, comprising the steps of:
   (a) extracting the proteinase inhibitor and other protein products from the plant tissue by preparing a mixture of solvent and comminuted plant tissue to form a solid fraction and a liquid fraction comprising the proteinase inhibitor and other protein products;
   (b) heating the liquid fraction to a temperature and for a time period sufficient to denature at least some of the other protein products without substantially denaturing the proteinase inhibitor;
   (c) removing the denatured protein products to prepare a clarified extract solution; and
   (d) measuring the amount of proteinase inhibitor present in the clarified extract.

2. The method of claim 1 wherein the solvent comprises formic acid and sodium chloride.

3. The method of claim 2 wherein the solvent comprises about 0.5% to about 2.5% formic acid and 0 to 3.0 N sodium chloride.

4. The method of claim 1 wherein heat treating the liquid fraction is conducted at between about 60° to about 90° C.

5. The method of claim 4 wherein heat treating the liquid fraction is conducted for between about 30 to about 180 minutes.

6. The method of claim 1 wherein the step of removing the denatured protein products is carried out by centrifugation.

7. The method of claim 1, further comprising the step of comparing the measured proteinase inhibitor content against a standard.

8. The method of claim 1, wherein the plant tissue is potato tubers.

9. The method of claim 1, wherein the proteinase inhibitor is Proteinase Inhibitor II.

10. A method that does not include a dialyzing step of selecting potatoes for use as raw materials in a process for the extraction of proteinase inhibitor from the potatoes, comprising the steps of:
   (a) extracting the proteinase inhibitor and other protein products from the potatoes by preparing a mixture of solvent and comminuted potato to form a solid fraction and a liquid fraction comprising the protease inhibitor and other protein products;
   (b) heating the liquid fraction to a temperature and for a time period sufficient to denature at least some of the other protein products without substantially denaturing the proteinase inhibitor;
   (c) removing the denatured protein products to prepare a clarified extract solution
   (d) measuring the amount of proteinase inhibitor present in the clarified extract; and
   (e) rejecting any potatoes that have a proteinase inhibitor content less than a selected standard.

* * * * *